United States Patent [19]

Iwakiri

[11] Patent Number: Plant 6,076

[45] Date of Patent: Jan. 5, 1988

[54] ASIAN PEAR TREE NAMED "SHIN LI"

[75] Inventor: Ben T. Iwakiri, Sacramento, Calif.

[73] Assignee: The Regents of the University of California, Berkeley, Calif.

[21] Appl. No.: 814,248

[22] Filed: Dec. 27, 1985

[51] Int. Cl.[4] ..... A01H 5/03
[52] U.S. Cl. ..... Plt./36
[58] Field of Search ..... Plt./36

*Primary Examiner*—Robert E. Bagwill
*Attorney, Agent, or Firm*—Townsend and Townsend

[57] ABSTRACT

An Asian pear tree which is of large to medium size, tall, upright to slightly spreading, open, vigorous, rapid growing, and hardy; foliated with large, wide, long, thick, leathery, ovate leaves having acuminate apices, a margin with sharply setose serration, and a petiole of medium length and thickness; blooms early with white, medium size, fertile flowers; and is an early, regular, and productive bearer of large to medium size, round-oblate, fruit having medium smooth, thick to medium thick, light green to yellowish green skin, and white flesh which is firm, tender, crispy, juicy, and sweet.

1 Drawing Figure

BACKGROUND OF THE VARIETY

Field of the Invention

In the conduct of an extensive plant breeding program, I originated a substantial number of new and distinct varieties of fruit trees, and which included the herein-claimed variety of Asian pear tree; such plant breeding program having been undertaken by me at the University of California, Davis, Yolo County, Calif., in its research nursery, and in one of its experimental orchards.

CLASSIFICATION OF THE VARIETY

The present variety of Asian pear tree (identified by test selection number "12-43") is embraced by Class 36, Plants, of the U.S. Patent Office Manual of classification.

PRIOR VARIETIES

Among existing varieties which are known to me, and mentioned herein, are the Asian pears Kikusui, Tsu Li, Ya Li, and Chojuro; and the domestic Bartlett.

ORIGIN OF THE VARIETY

The present variety of Asian pear tree was originated by me in the aforesaid experimental nursery and orchard as a cross between the Kikusui and Tsu Li varieties of Asian pears. A substantial number of the resulting seeds were initially grown in a greenhouse, then in the nursery, and later transplanted to an experimental orchard near Winters, Calif., where such seedlings were maintained under close and continuing observation. Upon bearing fruit, one of such seedlings evidenced certain novel and distinctive characteristics and was selected for asexual reproduction, with a view toward possible ultimate commercial introduction.

ASEXUAL REPRODUCTION OF THE VARIETY

Subsequent to its origination and selection as above, the herein-claimed variety of Asian pear tree was asexually reproduced by me by top-grafting on compatible pear seedlings in the aforesaid experimental orchard and, in maturity, the reproductions ran true to the original tree in all respects.

SUMMARY OF THE VARIETY

The herein-claimed variety of Asian pear tree is of large to medium size, tall, upright to slightly spreading, open, vigorous, rapid growing, and hardy; foliated with large, wide, long, thick, leathery, ovate leaves having acuminate apices, a margin with sharply setose serration, and a petiole of medium length and thickness; blooms early with white, medium size, fertile flowers; and is an early, regular, and productive bearer of large to medium size, round-oblate, fruit having medium smooth, thick to medium thick, light green to yellowish green skin, and white flesh which is firm, tender, crispy, juicy, and sweet.

The herein-claimed variety of Asian pear tree is further, and more particularly, characterized by a tree which is compatible with all pear rootstocks and grows more vigorously on them than other Asian pear varieties; blooms slightly after the Tsu Li and Ya Li varieties and more nearly with the Chojuro; by the production of fruit of such substantial size that considerably less thinning is required in comparison to other Asian pear varieties; by the production of fruit which is of excellent flavor with a faint trace of tartness, refreshingly mild, and excellent texture (soluble solids over 13%); the fruit being more pear-shaped than most Asian pear varieties, but slightly flatter than, and with finer flesh texture than Asian pear selection "12-44" which is the subject of my U.S. plant patent application Ser. No. 814,113 filed 12/27/85; and by fruit which has a long storage life at 32° F. while maintaining its flavor and firmness.

BRIEF DESCRIPTION OF THE DRAWING

The drawing is an illustration by photographic reproduction in color, of separate fruit of the variety; certain of the fruit being shown whole, while other fruit is half cut-away to expose the flesh.

DESCRIPTION OF THE VARIETY

The botanical details of the present new and distinct variety of Asian pear tree — with color definition in common color terms — are as follows:

Tree:

*Size.*—Large to medium.
*Vigor.*—Vigorous. Rapid growing.

*Growth.*—Upright. Slightly spreading. Tall. Open.
*Hardiness.*—Hardy.
*Production.*—Productive.
*Bearing.*—Regular bearer.

Trunk:
*Size.*—Medium.
*Texture.*—Medium.

Branches:
*Size.*—Medium.
*Texture.*—Smooth.
*Color.*—Brown undercolor, overlaid with a grayish white scarf skin.
*Lenticels.*—Number: Numerous. Size: Large. Texture: Raised. Rough.

Leaves:
*Size.*—Large. Long — average length — 14.1 cm. Wide — average width — 8.2 cm.
*Texture.*—Smooth.
*Form.*—Ovate. Aices acuminate.
*Thickness.*—Medium. Leathery.
*Color.*—Top side — Dark Green. Under side — Light green.
*Margin.*—Sharply setose seration.
*Petiole.*—Medium length — average — 2.5 cm. Medium thickness.

Flowers:
*Date of bloom.*—Early — usually 3rd week in March.
*Size.*—Medium.
*Color.*—White.
*Fertility.*—Fertile.

Fruit:
*Date of ripening.*—Usually first three weeks of September (at about flesh firmness of 7-8 lbs.).
*Tenacity.*—Hangs well on tree.
*Size.*—Large to medium. Average length — 75 mm. Average width — 82.8 mm.
*Form.*—Slightly variable. Round-Oblate. Irregular.
*Stem.*—Medium length — average — 3.0 cm. Medium thickness.
*Cavity.*—Acute. Medium depth. Medium breadth. Smooth. Furrowed. Angular.
*Calyx.*—May be deciduous, partly persistent or persistent. When calyx persistent: open, medium size. When calyx deciduous: Scarred area where sepals were attached is light brown and scaly.
*Lobes.*—When calyx persistent: separated at base, erect, connivent, medium length, narrow width, acute.
*Basin.*—When calyx persistent: medium depth, wide, surface smooth, furrowed, slightly angular. When calyx deciduous: deep, medium size, sides sloping, furrowed and angular, surface smooth.

Skin
*Thickness.*—Thick to medium.
*Texture.*—Medium smooth. Dull.
*Color.*—Light green to yellowish green when eating ripe.
*Dots.*—Numerous. Large to medium. Russet. Raised.

Flesh:
*Color.*—White.
*Texture.*—Firm. Medium. Crisp. Tender. Juicy.
*Flavor.*—Sweet. Subacid. Trace of tartness.
*Aroma.*—Distinct. Similar to Tsu Li.
*Quality.*—Best.

Core:
*Size.*—Medium to small. Open. Abaxile.

Core lines:
*Form.*—Clasping.

Calyx tube:
*Length.*—Medium.
*Width.*—Medium.
*Form.*—Urn-shaped.

Seed:
*Size.*—Medium.
*Form.*—Plump.
*Shape.*—Acuminate.

Use: Dessert. Kitchen. Market. Home.
Keeping quality: Good. Long storage life (five to six months at 32° F.).
Resistance to insects: Equivalent to other Asian pear varieties, and the Bartlett.
Resistance to diseases: Equivalent to other Asian pear varieties.
Shipping quality: Good.

The Asian pear tree and its fruit herein described may vary in slight detail due to climatic and soil conditions under which the variety may be grown; the present description being of the variety as grown in the Sacramento Valley of California.

I claim:

1. A new and distinct variety of Asian pear tree, substantially as illustrated and described, characteristically including — in comparison to other Asian pear varieties — more vigorous growth on the rootstock; blooming slightly after the Tsu Li and Ya Li and more nearly with the Chojuro; and the early, regular and productive bearing of large to medium size, round-oblate fruit having light green to yellowish green skin at maturity, and white flesh which is firm, tender, crispy, juicy, and sweet with a faint trace of tartness; the fruit having a storage life of five to six months at 32° F. while maintaining its flavor and firmness.

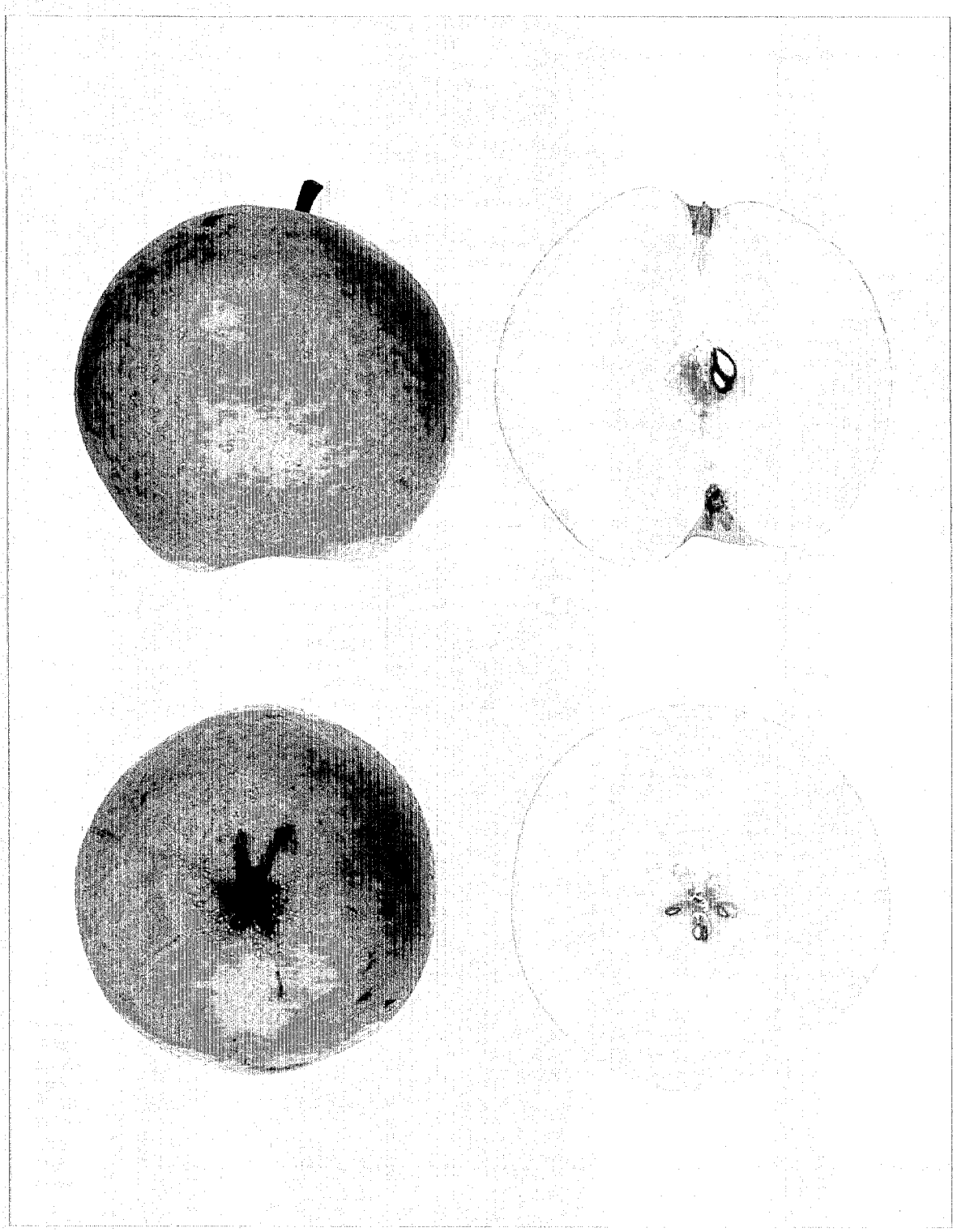

* * * * *